United States Patent [19]

Grabowski et al.

[11] Patent Number: 5,939,099
[45] Date of Patent: Aug. 17, 1999

[54] SOLID ACTIVE EXTRUSION COMPOUND PREPARATIONS CONTAINING LOW-SUBSTITUTED HYDROXYPROPYLCELLULOSE

[75] Inventors: Sven Grabowski, Ludwigshafen; Jörg Breitenbach, Mnnheim; Joerg Rosenberg, Ellerstadt; Axel Sanner, Frankenthal, all of Germany

[73] Assignee: BASF Aktiengesellschaft, Ludwigshafen, Germany

[21] Appl. No.: 08/875,514

[22] PCT Filed: Feb. 1, 1996

[86] PCT No.: PCT/EP96/00417

§ 371 Date: Jul. 30, 1997

§ 102(e) Date: Jul. 30, 1997

[87] PCT Pub. No.: WO96/25151

PCT Pub. Date: Aug. 22, 1996

[30] Foreign Application Priority Data

Feb. 14, 1995 [DE] Germany ............................ 195 04 832

[51] Int. Cl.⁶ .............................. A61K 9/10; A61K 47/38
[52] U.S. Cl. .............................................. 424/488; 514/781
[58] Field of Search ..................... 424/484, 488, 424/499, 468, 457; 264/464, 46.1

[56] References Cited

U.S. PATENT DOCUMENTS 4,801,460   1/1989   Goertz et al. .
4,880,585  11/1989   Klimesch et al. .
5,194,197   3/1993   Munk et al. .

FOREIGN PATENT DOCUMENTS 2014926  10/1990   Canada .
240 904  10/1987   European Pat. Off. .
240 906  10/1987   European Pat. Off. .
398 033  11/1990   European Pat. Off. .
544 144   6/1993   European Pat. Off. .

OTHER PUBLICATIONS

Chem. & Phar. Bul. vol. 42, No. 9, Matsumura et al., Computer Optimization for the Formulation of . . .
Chem. Pharm. Bull. 41(10) 1827–1831 (1993) Kawashima et al.
Chem. Abst. J5 8079–915.
Chem. Abst. J5 8192–817.

*Primary Examiner*—Edward J. Webman
*Attorney, Agent, or Firm*—Keil & Weinkauf

[57] ABSTRACT

Solid preparations are obtainable by melt extrusion of
 A) at least one active compound,
 B) a mixture of
  B1) from 10 to 90% by weight of a water-soluble, thermoplastic polymer, and
  B2) from 10 to 90% by weight of a low-substituted hydroxypropylcellulose, and
 C) from 0 to 50% by weight, based on the total amount of the preparation, of customary pharmaceutical auxiliaries.

2 Claims, No Drawings

SOLID ACTIVE EXTRUSION COMPOUND PREPARATIONS CONTAINING LOW-SUBSTITUTED HYDROXYPROPYLCELLULOSE

This application is a 371 of PCT/EP96/00417 filed Feb. 1, 1996.

The present invention relates to solid preparations, obtainable by joint melt extrusion of A) one or more active compounds, B) a mixture of B1) from 10 to 90% by weight of at least one thermoplastically processable, water-soluble polymer, and B2) from 10 to 90% by weight of a low-substituted water-insoluble hydroxypropylcellulose, and C) from 0 to 50% by weight, based on the total amount of the preparation, of one or more pharmaceutical auxiliaries.

The invention furthermore relates to a process for producing such preparations, and to their use as drugs.

Active compound-containing preparations which are produced by melt extrusion are generally known.

The extrusion of active compound-containing melts of water-soluble polymers, preferably of copolymers of vinylpyrrolidone, is described in EP-A 240 904 and EP-A 240 906.

JP-A 58-192817 and JP-A 58-79915 disclose the melt extrusion of active compound-containing preparations based on thermoplastic polymers such as hydroxypropylcellulose as binders.

Low-substituted hydroxypropylcellulose (L-HPC), which is prepared by partial etherification of cellulose with propylene oxide, is insoluble in water, but swells on contact with water. On account of this swelling behavior, L-HPC is employed as a disintegrant for accelerating the disintegration of the tablets. L-HPC can also be employed as a binder for tablets for increasing the tablet hardness.

Kawashima et al., Chem. Pharm. Bull. 41 (1933), 1827–31, describe that the use of L-HPC in granules for tableting is strongly dependent, on the one hand, on the particle size of the L-HPC, and on the other hand the active compound release profile is crucially affected by the pressing force during compaction.

In contrast to hydroxypropylcellulose having higher degrees of substitution, L-HPC, however, shows no thermoplastic processability.

It is an object of the present invention to find active compound preparations which can be produced by polymer-active compound melt extrusion and allow a specific adjustment of the release of active compound.

We have found that this object is achieved by the preparations defined at the outset, a process for their production, and their use as drugs.

Active compounds suitable as component A) are those which do not decompose under the processing conditions during melt extrusion.

Suitable active compounds are, for example:

acebutolol, acetylcysteine, acetylsalicylic acid, aciclovir, alprazolam, albumin, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydroxide, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidine, ceftriaxone, cefuroxime axetil, chloramphenicol, chlorhexidine, chlorpheniramine, chlorthalidone, choline, ciclosporin, cilastatin, cimetidine, ciprofloxacin, cisapride, cisplatin, clarithromycin, clavulanic acid, clomipramine, clonazepam, clonidine, clotrimazole, clozapine, codeine, colestyramine, cromoglicic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, domperidone, dopamine, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, folinic acid, furosemide, gemfibrozil, gentamicin, Ginkgo biloba, glibenclamide, glipizide, Glycyrrhiza glabra, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multi-vitamins and minerals, nystatin, N-methylephedrine, naftidrofuril, naproxen, neomycin, nicardipine, nicergoline, nicotinamide, nicotine, nicotinic acid, nifedipine, nimodipine, nitrendipine, nizatidine, norethisterone, norfloxacin, norgestrel, nortriptyline, ofloxacin, omeprazole, ondansetron, pancreatin, panthenol, pantothenic acid, paracetamol, penicillin G, penicillin V, phenobarbital, pentoxifylline, phenylephrine, phenylpropanolamine, phenytoin, piroxicam, polymyxin B, povidone-iodine, pravastatin, prazosin, prednisolone, propafenone, propranolol, pseudoephedrine, pyridoxine, quinidine, ramipril, ranitidine, reserpine, retinol, riboflavine, rifampicin, rutoside, saccharin, salbutamol, salcatonin, salicylic acid, selegiline, simvastatin, somatropin, sotalol, spironolactone, sucralfate, sulbactam, sulfamethoxazole, sulpiride, tamoxifen, tegafur, teprenone, terazosin, terbutaline, terfenadine, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, zidovudine.

Furthermore, suitable active compounds are also vitamins such as vitamin C, β-carotene and other carotenoids or crop protection agents.

The active compounds are preferably present in the form of solid solutions, ie. distributed in the matrix in molecularly disperse form, or in the form of a solid dispersion.

The amount of the active compound component A) in the total preparation can be varied within wide limits depending on the activity and release rate. The active compound content can thus be in the range from 0.1 to 90% by weight, preferably from 0.5 to 60% by weight, based on the total preparation. The only condition is that the preparation is still thermoplastically processable.

As polymeric components B), the preparations according to the invention contain a mixture of B1) from 10 to 90% by weight, preferably from 20 to 80% by weight, of a water-soluble, thermoplastic polymer, and B2) from 10 to 90% by weight, preferably from 20 to 80% by weight, of a water-insoluble low-substituted hydroxypropylcellulose, the quantitative data being based on the sum of the amounts of B1) and B2).

Water-soluble polymers B1) which may be mentioned are:

alkylcelluloses such as methylcellulose,
hydroxyalkylcelluloses such as hydroxymethyl-, hydroxyethyl-, hydroxypropyl- and hydroxybutylcellulose,
hydroxyalkylalkylcelluloses such as hydroxyethylmethyl- and hydroxypropylmethylcellulose,
polyvinylpyrrolidone,
copolymers of N-vinylpyrrolidone and vinyl acetate containing up to 50% by weight of vinyl acetate,
carboxyalkylcelluloses such as carboxymethylcelluloses,
polysaccharides such as alginic acid and their alkali metal and ammonium salts, and mixtures of such water-soluble polymers.

The component B1) should soften or melt in the total mixture of all components in the range from 50 to 180° C., preferably from 60 to 150° C., so that the material is extrudable. The glass transition temperature of the polymers should accordingly be below 180° C.

Water-soluble means that at least 0.5 g, preferably at least 2 g, of the polymer dissolve in 100 g of water at 20° C., if appropriate even in colloidal form.

Preferably, the polymer component A) used is hydroxypropylcellulose having a degree of molar substitution of from 3.0 to 4.4.

According to the invention, component B2) is a low-substituted hydroxypropylcellulose having a degree of molar substitution of from 0.5 to 2, preferably from 1.5 to 1.8, the low-substituted hydroxyproyplcellulose (L-HPC) as is described in the US Pharmacopeia/NF XVII and the Japanese Pharmacopeia JP XI. L-HPC of this type is water-insoluble, but swellable in water, and does not behave thermoplastically.

Within the limits indicated, the amount of component B2) employed preferably depends on what active compound release rate is desired. In the case of rapid release, the use of smaller amounts is recommended, for example from 5 to 30% by weight. In the case where a delayed release of active compound is desired, the use of from 30 to 90% by weight of B2) is recommended.

According to the invention, the particle size of the L-HPC employed is not critical.

As components C), the preparations according to the invention can contain the customary pharmaceutical auxiliaries such as fillers, lubricants, mold release agents, flow regulators, plasticizers, colorants and stabilizers in amounts of up to about 50% by weight. These and the amounts indicated in the following are in each case based on the total weight of the preparation (=100%).

Fillers which may be mentioned are, for example, the oxides of magnesium, aluminum, silicon and titanium and also lactose, mannitol, sorbitol, xylitol, pentaerythritol and its derivatives, the amount of filler being from about 0.02 to 50, preferably 0.2 to 20, % by weight.

Flow regulators which may be mentioned are, for example, the mono-, di- and triglycerides of the long-chain fatty acids such as $C_{12}$-, $C_{14}$-, $C_{16}$- and $C_{18}$-fatty acid, waxes such as carnauba wax and also the lecithins, the amount being from about 0.1 to 30, preferably 0.1 to 5, % by weight.

Plasticizers which may be mentioned are, for example, besides low molecular weight polyalkylene oxides such as polyethylene glycol, polypropylene glycol and polyethylene propylene glycol, also polyhydric alcohols such as propylene glycol, glycerol, pentaerythritol and sorbitol and also sodium diethylsulfosuccinate, the mono-, di- and triacetate of glycerol and polyethylene glycol stearic acid ester. In this case the amount of plasticizer is from about 0.5 to 15, preferably from 0.5 to 5, % by weight.

Lubricants which may be mentioned are, for example, stearates of aluminum or calcium and also talc and silicones, their amount being from about 0.1 to 5, preferably from 0.1 to 3, % by weight.

The stabilizers which may be mentioned are, for example, light stabilizers, antioxidants, radical scavengers and stabilizers against microbial attack, their amount preferably being from about 0.01 to 0.05% by weight.

In order to produce the preparations according to the invention, the active compound component can either be fused directly with the polymer B in the form of a physical mixture or mixed with the polymer melt already present.

Otherwise, the mixing of the component A) with the melt is carried out in a manner known per se in extruders, preferably in single- or double-screw extruders in a temperature range from 50 to 200° C. The shaping of the active compound-containing polymer melt to give the preparations according to the invention can be carried out, for example, by calendering of the extrudate according to the method described in EP-A 240 906 and also according to the processing method disclosed in DE-A 38 30 355 by comminution of the extrudate with rotating knives into pieces of equal volume, which are still deformable, having a solidified surface, and subsequent compression to give tablets in the customary tableting machines.

It is possible to mix the auxiliaries into the melt or solution of active compounds and polymers B. The auxiliaries can further be incorporated into the polymer melt together with the active compound. Additionally, mixtures of auxiliaries, the active compound and the polymers B can be directly fused. In general, it is customary to fuse a physical mixture of auxiliaries, active compounds and the polymers B jointly.

The preparations according to the invention are used as drugs and employed in the form of tablets, pellets, granules or capsules. Preferably, pharmaceutical forms having delayed release of active compound are produced using the preparations according to the invention.

If desired, the solid pharmaceutical form can also be provided with a customary coating to improve the appearance and/or the taste (coated tablet) or for the purpose of additional delay in the release of active compound. For tablets to be taken orally having a delayed release of active compound, it is favorable if the tablet is produced in closed-cell porous form according to one of the known techniques in order that it floats in the stomach and as a result resides there longer.

The present invention makes possible in a simple manner a specific adjustment of the active compound release profile of the solid pharmaceutical forms according to the invention, especially in the production of solid pharmaceutical forms having a delayed release of active compound. Surprisingly, this takes place independently of the particle size of the L-HPC and process parameters during shaping.

EXAMPLES 1 to 3

The amounts of active compound and the polymers B1) and B2) indicated in the table were mixed, introduced into a double-screw extruder (ZSK 30, Werner & Pfleiderer) and extruded over 5 temperature zones. The temperatures of the individual temperature zones (batches 1–5) are in each case indicated in Table I. The melt extrudates emerging through the extruder nozzle lip were pelleted by air-cooled heat reduction using a knife roll granulator.

The release of active compound was measured by means of the paddle method according to USP XXI, US Pharmacopeia. This in vitro method is used for the determination of the rate of solution of active compound-containing shaped articles (e.g. tablets, pellets etc.).

To do this, 900 ml of a phosphate buffer having a pH of 6.8 were temperature-controlled at 37° C. with 0.1% by weight of sodium lauryl sulfate in a 1 l vessel having a round bottom and 300 g of pellets of particle size from 1.25 to 1.60 mm were added. The release of active compound from the pellets was determined by UV spectroscopy at a speed of rotation of the paddle of 100 rpm after 1, 2, 3, 4, 5, 6, 7 and 8 hours in each case.

The results of this test are shown in Table II.

TABLE I

| Example | Nifedipine % by wt. | Polymer B1)[1] % by wt. | Polymer B2)[2] % by wt. | Temperature batches 1–5 |
|---|---|---|---|---|
| 1 | 20 | 50 | 30 | 70, 120, 110, 100, 100 |
| 2 | 20 | 40 | 40 | 60, 120, 120, 110, 120 |
| 3 | 20 | 30 | 50 | 60, 120, 120, 120, 130 |

[1] Hydroxypropylcellulose having a degree of molar substitution of from 3.0 to 4.4 (Klucel EF, Hercules, USA)
[2] Hydroxypropylcellulose having a degree of molar substitution

TABLE II

| | Release in % after hours | | | | | | | |
|---|---|---|---|---|---|---|---|---|
| Example | 1 | 2 | 3 | 4 | 5 | 6 | 7 | 8 |
| 1 | 32 | 70 | 91 | 99 | 100 | 100 | 100 | 100 |
| 2 | 31 | 60 | 77 | 89 | 96 | 100 | 100 | 100 |
| 3 | 24 | 43 | 57 | 69 | 75 | 81 | 87 | 91 |

We claim:

1. A solid pharmaceutical composition obtained by joint melt extrusion of
   A) one or more active compounds, and
   B) a mixture of
      B1) from 10 to 90% by weight of a water-soluble hydroxypropylcellulose, and
      B2) from 10 to 90% by weight of a low-substituted water-insoluble hydroxypropylcellulose, and
   C) from 0 to 50% by weight, based on the total amount of the preparation of one or more pharmaceutical auxiliaries.

2. A process for producing the composition defined in claim 1, which process comprises processing the active compound component A) with the polymeric component B) and the auxiliaries C) to give a melt, extruding the melt and shaping the extruded melt.

* * * * *